United States Patent [19]

Commeyras et al.

[11] 4,001,081

[45] Jan. 4, 1977

[54] PROCESS FOR THE PREPARATION OF AMIDES BY BIOLOGICAL HYDROLYSIS

[75] Inventors: Auguste Commeyras, Clapier; Alain Arnaud, Clermont L'Herault; Pierre Galzy; Jean-Claude Jallageás, both of Montpellier, all of France

[73] Assignee: Agence Nationale de Valorisation de la Recherche (ANVAR), Neuilly sur Seine, France

[22] Filed: Dec. 17, 1975

[21] Appl. No.: 641,774

[30] Foreign Application Priority Data

Dec. 18, 1974 France .............................. 74.41828

[52] U.S. Cl. .................................................. 195/29
[51] Int. Cl.$^2$ ........................................ C12D 13/06
[58] Field of Search ................... 195/29, 50, 29.50

[56] References Cited

UNITED STATES PATENTS 3,940,316    2/1976    Commeyras et al. ................ 195/50

OTHER PUBLICATIONS

Robinson et al. "Ricinine Nitrilase" in Methods in Enzymology vol. XVII Part B pp. 244–248 (1971).

*Primary Examiner*—Lionel M. Shapiro
*Attorney, Agent, or Firm*—Donald D. Jeffery

[57] ABSTRACT

The present invention relates to a process for the preparation of amides.

This process for the preparation of an amide by hydrolysis of the corresponding nitrile is characterized in that the said nitrile in aqueous solution is subjected to the action of bacteria having a nitrilasic activity, in that the pH of the said aqueous solution is maintained at a value at least equal to the limiting pH of the amide hydrolysis reaction, and in that the bacteria mass is separated from the amide solution.

This process is useful in particular for the preparation of acrylamides.

12 Claims, No Drawings

PROCESS FOR THE PREPARATION OF AMIDES BY BIOLOGICAL HYDROLYSIS

The present invention relates to a process for the preparation of amides by biological hydrolysis of the corresponding nitriles.

For the preparation of amides of great economic importance such as acrylamide and methacrylamide, it has already been proposed to prepare them by chemical hydrolysis of the corresponding nitriles.

The processes known hitherto for carrying out the hydrolysis of the nitriles into amides are principally of two types:

a. hydration in a very acid medium, for example in the presence of 60% sulphuric acid, thus the yields of these processes never exceed 80% and the product obtained contains large quantities of secondary products which makes purification difficult and thus onerous. The presence of sulphuric acid in large quantity in relation to the nitriles in addition necessitates a neutralisation stage when the amide is recovered;

b. recently metallic catalysts have been used containing copper for example, and this application has permitted the improvement of the yield to 95%. However, this process remains difficult to implement because the catalysts used are not reproducible. In addition it is still necessary to apply a purification stage as in the preceding process.

Therefore in all these cases we have non- quantitative, onerous processes of which the final product is often difficult to isolate from the reaction medium. Furthermore these processes are not always applicable since certain nitriles are resistant to chemical hydrolysis.

The present invention proposes a practically quantitative process which permits the hydrolysis of virtually all nitriles in mild conditions which are particularly interesting when fragile compounds are being treated, the said process itself being extremely simple to implement and the separation of the amide obtained from the reaction medium being possible without any difficulty.

In the process according to the invention an amide is prepared by hydrolysis of the corresponding nitrile by subjecting the said nitrile in aqueous solution to the action of bacteria having a nitrilasic activity and by maintaining the pH of the said aqueous solution at a value at least equal to the limiting pH of the amide hydrolysis reaction, and then by separating the bacterial substance from the amide solution.

It may be useful to mention that a bacteria having a nitrilasic activity which can be used in the process according to the present invention is a bacteria which has at least one nitrilase capable of catalysing the hydrolysis of a nitrile into amide.

The limiting pH of the amide hydrolysis reaction is defined as being the pH below which there is formed in the aqueous solution a large quantity of acid corresponding to the nitrile. This limiting pH of the amide hydrolysis reaction in general corresponds to the inhibition pH of the amidase but in certain cases it can be lower than this inhibition pH and may be determined experimentally as a function of the nature of the nitrile and the strain used. The strains used in the process are preferably more particularly strains of selected bacteria which develop on a medium containing 1.17% of Yeast Carbon Base Difco, 0.1% acetonitrile and 2.5% gelose. Such a medium poured in a sterile Petri dish by feeding with various sources of germs such as earths, waters or industrial waste permits the isolation of colonies which proliferate, their purification by dilution and spreading out on the same medium and after selection it is possible to obtain strains which can be used in the process according to the invention. The nitrilasic activity bacteria used in the process according to the invention are selected preferably from the genera Bacillus, Bacteridium in the sense of Prévot, Micrococcus and Brevibacterium in the sense of Bergey.

More preferably still, the bacteria are selected from the strains registered in the Collection of the Chair of Genetics of the Ecole nationale supérieure Agronomique de Montpellier under the numbers R 332, R 340, R 341, A 111, B 222, A 112, A 13, A 141, A 142, B 211, B 212, B 221, C 211, R 21, R 22, R 311, R 312, R 331 and in the Centraal Bureau voor Schimmelcultures in Delft under the numbers C 211 CBS 499.74, R 312 CBS 717.73, B 222 CBS 498.74, A 111 CBS 497.74, R 341 CBS 496.74, R 340 CBS 495.74, R 332 CBS 494.74, and which have the morphological and physiological characteristics described in Table I and II.

The above mentioned strains are suitable to give successively the following reactions:

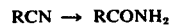

$$RCN \rightarrow RCONH_2 \qquad 1$$

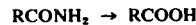

$$RCONH_2 \rightarrow RCOOH \qquad 2$$

However it has been observed that the optimum pH value and the limiting pH value are not the same for these two stages and in particular that there is a pH value for limiting the amide hydrolysis reaction above which only reaction 1 takes place.

For this reason, in a preferred embodiment of the process according to the present invention, the pH of the solution is basic and near to 9.

The solution is made basic by the addition of organic or inorganic basis such as soda and ammonia. In certain cases, in particular for the preparation of acrylamide, the limiting pH of the amide hydrolysis reaction is lower and the reaction can be carried out at a pH of between 7 and 9.

It should be noted that when the nitriles used are α-hydroxylated or α-aminated, it is not possible to determine a limiting pH for the amide hydrolysis reaction and that a certain quantity of acid always forms in the reaction medium.

In the preferred embodiment of the process according to the invention, the aqueous solution contains between 1 and 30 % by weight approximately of nitrile, but in a variant of the method of the process, the nitrile is added continuously or discontinuously during the reaction. The bacteria are present in the solution preferably in a quantity of between 10 and 50 g of bacteria by dry weight per liter of solution. In the optimum conditions defined above, the reaction is total after approximately 1 hour and frequently less.

The strains according to the present invention can be preserved on a medium containing mineral material, ammonia, vitamins and glucose, such as glucose-treated yeast nitrogen base Difco. But for the preservation and culture of these strains it is also possible to use hexadecanes or gas-oils (permitting the removal of paraffin) as a hydrocarbonated source or lactoserum, which constitutes an advantage, since these are cheap materials available in large quantities.

The nitrilasic activity of the strains selected by the preceding process is very general. Thus the strains described in the present application are capable of hydrolysing almost without distinguishing the following types of compounds:

simple nitriles such as acetonitrile, isobutyronitrile;
α-aminated nitriles such as α-aminopropionitrile, α-aminoγ-methylthiobutyronitrile, α-aminobutyronitrile, aminoacetonitrile;
α-hydroxylated nitriles such as lactonitrile, hydroxyaceto nitrile, α-hydroxy-γ-methylthiobutyronitrile;
β-aminated nitriles such as amino-3-propionitrile;
dinitriles such as malonitrile, succinonitrile, adiponitrile;
α-unsaturated nitriles such as acrylonitrile, methacrylonitrile;
α-benzenic nitriles such as homoveratric nitrile, benzonitrile;
heterocyclic nitriles such as nicotinonitrile, isonicotinonitrile.

By the above described process the applicant has isolated the 18 strains mentioned above, having a nitrilasic activity which is of particular interest for the implementation of the process. These strains have the following common characteristics:

Positive Gram; negative alcohol-acid resistance.
Strict aerobiosis; positive catalase.
Use of glucose, saccharose, maltose and lactose by oxidation without production of gas and without acidification.

TABLE I

| STRAIN | SPORE | MOBILITY | CELLULAR MORPHOLOGY | MORPHOLOGY OF COLONIES |
|---|---|---|---|---|
| R 332 | + | low | rods (1.8–3.6)μ × 0.9 μ | Circular, smooth, convex, pink, with solid edges. |
| R 340 | + | − | rods 2.7μ × 0.9μ | Circular, small, white, with diffuse edges. |
| R 341 | + | − | rods 2.7μ × 0.9μ | Large, very granulous, white, flat. |
| A 111 | − | − | shells 0.9 with 1.8μ | Circular, small, wrinkled, convex, pink with lobed edges. |
| B 222 | − | + | rods (3.6–4.5)μ × 0.9μ | Circular, small, yellow-orange colour. |
| A 112 | − | low | rods (1.8–3.6)μ × 0.9μ | Small, opaque, in relief, with lobed edges, pink-orange. |
| A 13 | − | low | rods 2.2μ × 0.9μ | Circular, smooth, opaque, orange-pink, with solid edges. |
| A 141 | − | − | rods (1.8–3.6)μ × 0.9μ | Small, almost flat, opaque, granulous, orange-pink, with lobed edges. |
| A 142 | − | − | rods (3.6–4.5)μ × 0.9 μ | Circular, smooth, opaque, orange with solid edges. |
| B 211 | − | − | rods 1,8μ × 0.9μ | Circular, convex, small, smooth, pink, with solid edges. |
| B 212 | − | − | rods 3.6μ × 0.9μ | Circular, convex, smooth, pink with solid edges. |
| B 221 | − | low | rods (3.6–4)μ × 0.9 μ | Circular, very lobed, in relief, yellow-orange colour. |
| C 211 | − | low | rods (3.6–8.1)μ × 0.9 μ | Circular, smooth, shining, pink, with solid edges. |
| R 21 | − | − | rods 5.4μ × 0.9μ | Circular, flat, pink, granulous, with slightly lobed edges. |
| R 22 | − | low | rods 2.7μ × 0.9 μ | Circular, smooth, orange, in relief with solid edges. |
| R 311 | − | low | rods (1.8–3.6)μ × 0.9 μ | Circular, yellow, in relief, with solid edges. |
| R 312 | − | − | rods (4.5–9)μ × 0.9 μ | Circular, convex, yellow, with solid edges. |
| R 331 | − | − | rods 4.5 μ × 0.9 μ | Circular, pink, flat, diffuse and opaque. |

TABLE II

PRINCIPAL PHYSIOLOGICAL CHARACTERISTICS

| STRAIN | OXYDASE TEST | INDOLE | CITRIC ACID USE | EGG-WHITE HYDROLYSIS | OPTIMUM pH | ACETYL-METHYL CARBINOL PRODUCTION |
|---|---|---|---|---|---|---|
| R 332 | − | − | − | − | 6.5 | high |
| R 340 | − | + | + | − | 6.5 | — |
| R 341 | − | + | − | − | 6.0 | — |
| A 111 | − | + | + | slight | 6.5 | low |
| B 222 | + | − | + | − | 6.0 | — |
| A 112 | − | + | + | − | 6.5 | — |
| A 13 | − | + | − | − | 6.0 | low |
| A 141 | − | − | + | − | 6.5 | low |
| A 142 | − | + | + | − | 6.0 | low |
| B 211 | − | + | + | − | 6.5 | high |
| B 212 | − | − | + | + | 6.0 | — |
| B 221 | − | + | + | − | 6.5 | — |
| C 211 | − | + | − | − | 6.0 | — |
| R 21 | − | + | + | − | 7.5 | — |
| R 22 | − | + | + | − | 6.0 | — |
| R 311 | − | + | + | − | 6.0 | low |
| R 312 | − | − | + | slight | 6.0 | — |
| R 331 | − | + | − | + | 6.0 | — |

No strain is formed from alcohol. Starch is not hydrolized but there is a growth on potato.
Test for tyrosinase on potato negative.
vitamin requirement.
Absence of hydrolysis of gelatine.
Growth on ammonia and on nitrates as only source of nitrogen.
No release of hydrogen sulphide.
Absence of growth in the presence of hyper-salted broth.

All the strains give off ammmonia after culture on nitrates; in addition they give nitrites except for the strains B 221, B 211, B 212 and C 211, Strain B 222 releases gas from nitrates.

The strain R 332 belongs to the genus Bacillus, but has a low proteolytic activity. The strains B 340 and R 341 are close to the genus Bacteridium in the sense of Prevot. The other strains are asporulated. The strain A 111 is a Micrococcus. All the other strains are close to the genus Brevibacterium in the sense of Bergey. It should be noted that the strain B 222 is very close to *Brevibacterium imperiale*.

Although in certain cases the low solubility in water of the nitrile poses a problem, this does not noticeably hinder the nitralasic activity of the bacteria which can be used in the process according to the invention.

An advantage of the process according to the invention is that it is possible to recycle the bacteria which are still active at the end of the process. In addition certain of the bacteria belong to physiological types which have already been fixed on support.

Obviously the processes described do not require the growth of the bacteria and it is therefore possible to use if desired acellular enzyme preparations, but in this case, the cost price of the process increases considerably since it requires the extraction of the enzyme. Nevertheless in the present description and in the claims "bacteria having a nitralasic activity" should be taken to mean both the bacteria and the corresponding acellular enzyme preparations.

A few examples of the industrial application of the process according to the invention will be given below in order to illustrate and to show certain aspects of the use of the invention without however in any way limiting it.

These embodiments of the process according to the present invention have all been carried out using the strain R 312 registered in the Collection of the Chair of Genetics of the Ecole nationale superieure agronomique de Montpellier and also at the Centraal Bureau voor Schimmelcultures in Delft under number CBS 717,73. These examples are in particular intended to show the non-specificity of the strains selected, and this is why they have all been carried out with the strain R 312, however, virtually all the strains selected are capable of effecting the hydrolyses described hereinafter.

EXAMPLE 1

Preparation of acetamide

Strain R 312 is cultivated on a medium containing glucose as a source of carbon. After growth, the cells are centrifuged, washed with physiological water then placed in suspension in the reaction medium constituted by a 5% solution by weight of acetonitrile. The pH is adjusted to 9 using potash or ammonia. The bacteria cells representing approximately 20 to 40 g of dry material per liter effect the total hydrolysis of the nitrile into amide in 1 to 2 hours at 25°C under agitation, the pH being maintained constant at 9. They are then eliminated by centrifuging. The supernatant contains acetamide which can be recovered by chloroform extraction.

EXAMPLE 2

Preparation of isobutyramide

As in the preceding example, the strain R 312 is cultivated on a medium containing glucose as the carbon source. After growth, the cells are centrifuged, washed in physiological water then placed in suspension in the reaction medium which is constituted by an aqueous solution of 5% by weight of isobutyronitrile. The pH is adjusted to 9 with potash or ammonia. The bacteria cells representing approximately 20 to 40 g of dry material per liter effect the total hydrolysis of the nitrile into amide in 20 to 40 minutes at 25° C under agitation, the pH being maintained constant at 9. They are then eliminated by centrifuging. The supernatant contains isonicotinamide which can be recovered by cold crystallisation.

EXAMPLE 3

Preparation of isonicotinamide

The strain R 312 is cultivated on a medium containing glucose as the carbon source. After growth the cells are centrifuged, washed in physiological water then placed in suspension in a reaction medium constituted by a 5% aqueous solution by weight of isonicotinonitrile. The pH is adjusted to 9 using ammonia and potash. The bacteria cells representing approximately 20 to 40 g of dry material per liter effect the total hydrolysis of the nitrile into amide in 20 to 40 mins at 25° C under agitation, the pH being maintained constant at 9. They are then eliminated by centrifuging. The supernatant contains the isonicotinamide which can be recovered by cold crystallisation.

EXAMPLE 4

Preparation of benzamide

The strain R 312 is cultivated on a medium containing glucose as the carbon source. After growth the cells are centrifuged, washed in physiological water then placed in suspension in a reaction medium constituted by an aqueous solution of 5% by weight of benzonitrile. The pH is adjusted to 9 with ammonia or potassium. The bacteria cells representing approximately 20 to 40 g of dry material per litre effect the total hydrolysis of the nitrile into amide in 30 to 40 minutes at 25° C under agitation, the pH being maintained constant at 9. They are then eliminated by centrifuging. The supernatant contains the benzamide which can be recovered by extraction.

EXAMPLE 5

Preparation of succinamide

The strain R 312 is cultivated on a medium containing glucose as the source of carbon. After growth the cells are centrifuged, washed in physiological water then placed in suspension in a reaction medium constituted by an aqueous solution of 1% by weight of succinonitrile. The pH is adjusted to 9 with ammonia or potassium. The bacteria cells representing approximately 20 to 40 g of dry material per liter effect the total hydrolysis of the nitrile into amide in 20 to 40 minutes at 25° C under agitation, the pH being maintained constant at 9. They are then eliminated by centrifuging. The supernatant contains the succinamide which may be recovered by cold precipitation.

EXAMPLE 6

Preparation of acrylamide

The strain R 312 is cultivated on a medium containing glucose as the carbon source. After growth the cells are centrifuged, washed in physiological water, then placed in suspension in a reaction medium constituted by an aqueous solution of 12% by weight of acrylonitrile. The pH is maintained at 9 using ammonia. The bacteria cells representing approximately 20 to 40 g of dry material per liter effect the total hydrolysis of the nitrile into amide in 20 to 30 minutes at 25° C under agitation, the pH being maintained constant at 9. They are then eliminated by centrifuging. The supernatant contains the acrylamide which can be recovered by chloroform extraction. Provided certain precautions are taken and the acrylonitrile is added progressively, it is possible to attain a final acrylamide concentration of 20% by weight.

EXAMPLE 7

Variant of Example 6

In the case of acrylonitrile, it is possible to stop the reaction at the amide stage, at pH values lower than 9, which is not the case with all the products tested. The operation described in Example 6 can be carried out at pH 7 to 9.

EXAMPLE 8

Preparation of methacrylamide

The strain R 312 is cultivated on a medium containing glucose as the carbon source. After growth the cells are centrifuged, washed in physiological water, then placed in suspension in a reaction medium constituted by an aqueous solution of 8% by weight of methacrylonitrile. The pH is maintained at 9 using ammonia. The bacteria cells representing approximately 20 to 40 g of dry material by liter effect the total hydrolysis of the nitrile into amide in 20 to 30 minutes at 25° C under agitation, the pH being maintained constant at 9. They are then eliminated by centrifuging. The supernatant contains the methacrylamide which can be recovered by chloroform extraction.

EXAMPLE 9

Variant of Example 8

In the case of methacrylonitrile, it is possible to stop, as in that of acrylonitrile, the reaction at the amide stage, at pH values lower than 9, which is not the case with all the products tested. The operation described in Example 8 can be carried out at pH 7 to 9.

EXAMPLE 10

Preparation of nicotinamide

The strain R 312 is cultivated in a medium containing glucose as the carbon source. After growth the cells are centrifuged, washed in physiological water, then placed in suspension in a reaction medium constituted by an aqueous solution of 5% by weight of nicotinonitrile. The pH is adjusted to 9 using ammonia or potash. The bacteria cells representing approximately 20 to 40 g of dry material per liter effect the total hydrolysis of the nitrile in to amide in 20 to 40 minutes at 25° C under agitation, the pH being maintained constant at 9. They are then eliminated by centrifuging. The supernatant contains the nicotinamide which can be recovered by cold crystallization.

EXAMPLE 11

Preparation of adipamide

The strain R 312 is cultivated on a medium containing glucose as the carbon source. After growth the cells are centrifuged, washed in physiological water then placed in suspension in the reaction medium constituted by a solution of 5% by weight of adiponitrile. The pH is adjusted to 9 using potassium or ammonia. The bacteria cells representing approximately 20 to 40 g of dry material per liter effect the total hydrolysis of the nitrile into amide in 30 minutes at 25° C under agitation, the pH being maintained constant at 9. They are then eliminated by centrifuging. The supernatant contains adipamide which can be recovered by chloroform extraction.

EXAMPLE 12

Variant of Examples 1 to 11

The strain R 312 can also be cultivated on lacto-serum or on a synthetic medium containing paraffins as the carbon source.

Naturally, as is clearly shown by the Examples, the bacteria mass can be separated from the reaction solution by all the known means, such as centrifuging.

Similarly for the extraction of the amide formed it is possible to have recourse to all the processes known in this technique.

We claim:

1. A process for the preparation of an amide by hydrolysis of the corresponding nitrile, characterized in that the said nitrile in aqueous solution is subjected to the action of bacteria having a nitrilasic activity, in that the pH of the said aqueous solution is maintained at a value at least equal to the limiting pH of the amide hydrolysis reaction, then in that the bacteria mass is separated from the amide solution.

2. A process according to claim 1 characterized in that selected bacteria are used which develop on a medium containing 1.17% of Yeast Carbon Base Difco, 0.1% acetonitrile and 2.5% gelose.

3. A process according to claim 1 and characterized in that the bacteria are selected from the genera Bacillus, Bacteridium in the sense of Prevot, Micrococcus and Brevibacterium in the sense of Bergey.

4. A process according to claim 1 characterised in that the bacteria are chosen from among the strains numbers R 332, R 340, R 341, A 111, B 222, A 112, A 13, A 141, A 142, B 211, B 212, B 221, C 211, R 21, 22, 22, R 311, R 312, R 331 registered at the Chair of Genetics of the Ecole nationale supéricure Agronomique de Montpellier and having the morphological and physiological characteristics described in Tables I and II of the specification.

5. A process according to claim 1, characterized in that a strain is used which has been chosen from among the strains registered at the Centraal Bureau voor Schimmelcultures in Delft under the numbers C 211 CBS 499.74, R 312 CBS 717.73, B 222 CBS 498.74, A 111 CBS 497.74, R 341 CBS 496.74, R 340 CBS 495.74, 332 332 CBS 494.74.

6. A process according to claim 1 characterized in that the pH of the aqueous solution is maintained at a value greater than 8.

7. A process according to claim 6, characterized in that the pH of the aqueous solution is maintained at a value close to 9.

8. A process according to claim 1 characterized in that the aqueous solution contains a nitrile acrylonitrile or methacrylonitrile and that the pH of the solution is maintained at a value greater than 7.

9. A process according to claim 1, characterized in that the aqueous solution contains between 1 30% by weight of nitrile.

10. A process according to claim 1, characterized in that the aqueous solution contains between 10 and 50 g of bacteria by dry weight per liter.

11. A process according to claim 1, characterized in that the nitrile is added continuously to the aqueous solution during hydrolysis.

12. A process according to claim 1, characterized in that the bacteria mass is separated from the amide solution by centrifuging.

* * * * *